United States Patent [19]

Coates et al.

[11] Patent Number: 4,695,578
[45] Date of Patent: Sep. 22, 1987

[54] 1,2,3,9-TETRAHYDRO-3-IMIDAZOL-1-YLMETHYL-4H-CARBAZOL-4-ONES, COMPOSITION CONTAINING THEM, AND METHOD OF USING THEM TO TREAT NEURONAL 5HT FUNCTION DISTURBANCES

[75] Inventors: Ian H. Coates, Hertfordshire; James A. Bell, Royston; David C. Humber, Ealing; George B. Ewan, Gerrard's Cross, all of England

[73] Assignee: Glaxo Group Limited, London, England

[21] Appl. No.: 931,032

[22] Filed: Nov. 17, 1986

Related U.S. Application Data

[63] Continuation of Ser. No. 820,743, Jan. 22, 1986, abandoned, and a continuation-in-part of Ser. No. 694,790, Jan. 25, 1985, abandoned.

[30] Foreign Application Priority Data

| Jan. 25, 1984 [GB] | United Kingdom | 8401888 |
| Oct. 15, 1984 [GB] | United Kingdom | 8425959 |
| Jan. 23, 1985 [GB] | United Kingdom | 8501727 |
| Jan. 23, 1985 [GB] | United Kingdom | 8501728 |

[51] Int. Cl.$^4$ .................. A61K 31/415; C07D 403/06
[52] U.S. Cl. .................................. 514/397; 548/336
[58] Field of Search ........................ 548/336; 514/397

[56] References Cited

U.S. PATENT DOCUMENTS

| 3,634,420 | 1/1972 | Littell et al. | 546/200 |
| 3,740,404 | 6/1973 | Littell et al. | 546/200 |
| 4,334,070 | 6/1982 | Berger et al. | 546/70 |
| 4,496,572 | 1/1985 | Cross et al. | 548/336 |

FOREIGN PATENT DOCUMENTS

| 901576 | 7/1985 | Belgium. | |
| 115607 | 8/1984 | European Pat. Off. | 546/200 |
| 1108578 | 4/1968 | United Kingdom | 546/200 |
| 1201061 | 8/1970 | United Kingdom | 546/200 |

OTHER PUBLICATIONS

Evans, Aust. J. Chem., 26(11), pp. 2555–2558 (1973).
Littell et al., J. Med. Chem., 15(8), pp. 875–876 (1972).

*Primary Examiner*—Alan L. Rotman
*Assistant Examiner*—Kurt G. Briscoe
*Attorney, Agent, or Firm*—Bacon & Thomas

[57] ABSTRACT

The invention relates to compounds of formula (I).

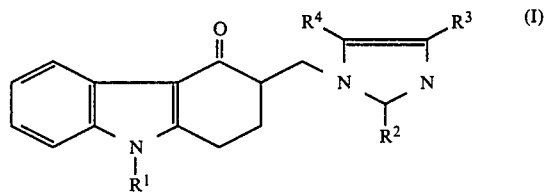

wherein $R_1$ represents a hydrogen atom or a $C_{1-10}$ alkyl, $C_{3-7}$ cycloalkyl, $C_{3-6}$ alkenyl, $C_{3-7}$ cycloalkyl-($C_{1-4}$) alkyl, $C_{3-10}$ alkynyl, phenyl or phenyl-$C_{1-3}$ alkyl group, and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-($C_{1-3}$) alkyl group and each of the other two groups, which may be the same or different, represents a hydrogen atom or a $C_{1-6}$ alkyl group; and physiologically acceptable salts and solvates, e.g. hydrates thereof.

The compounds are potent selective antagonists at "neuronal" 5-hydroxytryptamine receptors and are useful in the treatment of migraine and psychotic disorders such as schizophrenia.

20 Claims, No Drawings

1,2,3,9-TETRAHYDRO-3-IMIDAZOL-1-YLMETH-YL-4H-CARBAZOL-4-ONES, COMPOSITION CONTAINING THEM, AND METHOD OF USING THEM TO TREAT NEURONAL 5HT FUNCTION DISTURBANCES

This application is a continuation of application Ser. No. 820,743, filed Jan. 22,1986, and a continuation in-part of Ser. No. 694,790, filed Jan. 25, 1985, both abandoned.

This invention relates to heterocyclic compounds, to processes for their preparation, to pharmaceutical compositions containing them and to their medical use. In particular the invention relates to compounds which act upon certain 5-hydroxytryptamine (5HT) receptors.

5HT, which occurs endogenously in abundance in peripheral nerves and in blood platelets, is known to cause pain in man through a specific action on 5Ht receptors situated on terminals of primary afferent nerves. Compounds which antagonise the neuronal effects of 5HT have been shown to possess analgesic activity, for example, to relieve the pain of migraine. 5HT also causes depolarisation of the rat isolated vagus nerve preparation through the same 5HT-receptor mechanism, and inhibition of this effect correlates with an analgesic effect in vivo.

5HT also occurs widely in neuronal pathways in the central nervous system and disturbance of these 5HT containing pathways is known to alter behavioural syndromes, such as mood, psychomotor activity, appetite and memory. Since 'neuronal' 5HT- receptors of the same type as those present on primary afferent terminals are also present in the central nervous system, it is believed that compounds which antagonise the neuronal effects of 5HT will be useful in the treatment of conditions such as schizophrenia, anxiety, obesity and mania.

Existing treatments for such conditions suffer from a number of disadvantages. Thus, for example, known treatments for migraine include the administration of a vasoconstrictor such as ergotamine, which is non-selective and constricts blood vessels throughout the body. Ergotamine, therefore, possesses undesirable, and potentially dangerous, side effects. Migraine may also be treated by administering an analgesic such as aspirin or paracetamol, usually in combination with an antiemetic such as metaclopramide, but these treatments are of only limited value.

Similarly, existing treatments ffor psychotic disorders such as schizophrenia exhibit a number of serious side effects such as extrapyramidal side effects.

There is thus need for a safe and effective drug for the treatment of conditions where disturbance of 5HT containing pathways is involved, sych as migraine or psychotic disorders such as schizophrenia. It is believed a compound which is a potent and selective antagonist at 'neuronal' 5HT receptors will fulfil such a role.

We have now found a group of 3-imidazolylmethyl-tetrahydrocarbazolones which are potent and selective antagonists at 'neuronal' 5HT receptors.

The present invention provides a tetrahydrocarbazolone of the general formula (I):

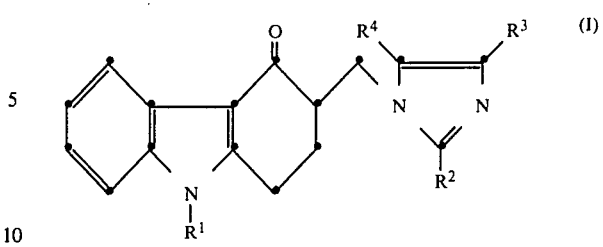

wherein $R^1$ represents a hydrogen atom or a $C_{1-10}$ alkyl, $C_{3-7}$ cycloalkyl, $C_{3-6}$ alkenyl, $C_{3-7}$ cycloalkyl-$(C_{1-4})$ alkyl, $C_{3-10}$ alkynyl, phenyl or phenyl-$C_{1-3}$ alkyl group, and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-$C_{1-3}$alkyl group and each of the other two groups, which may be the same or different, represents a hydrogen atom or a $C_{1-6}$ alkyl group; and physiologically acceptable salts and solvates, e.g. hydrates, thereof.

A preferred class of compounds within the scope of general formula (I) is that wherein $R^1$ represents a hydrogen atom or a $C_{1-10}$ alkyl, $C_{3-7}$ cycloalkyl, $C_{3-6}$ alkenyl, phenyl or phenyl-$C_{1-3}$alkyl group, and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl-$C_{1-3}$alkyl group and each of the other two groups, which may be the same or different, represents a hydrogen atom or a $C_{1-6}$ alkyl group; and physiologically acceptable salts and solvates, e.g. hydrates, thereof.

It will be understood that when $R^1$ represents a $C_{3-6}$ alkenyl group or a $C_{3-10}$ alkynyl group, the double or triple bond may not be adjacent to the nitrogen atom.

Referring to the general formula (I), the alkyl groups represented by $R^1$, $R^2$, $R^3$ and $R^4$ may be straight chain or branched chain alkyl groups, for example, methyl, ethyl, propyl, prop-2-yl, butyl, but-2-yl, 2-methlprop-2-yl, pentyl, pent-3-yl or hexyl.

An alkenyl group may be, for example, a propenyl group.

A phenyl-$C_{1-3}$ alkyl group may be, for example, a benzyl, phenethyl or 3-phenylpropyl group.

A cycloalkyl group may be, for example, a cyclopentyl, cyclohexyl or cycloheptyl group.

A $C_{3-7}$ cycloalkyl-$(C_{1-4})$ alkyl group may be for example a cyclopropylmethyl, cyclopentenylpropyl or a cycloheptylmethyl group. When the cycloalkyl moiety contains 5,6, or 7 carbon atoms it may optionally contain one or two double bonds, and may be for example a cyclohexenyl or cyclohexadienyl group.

A $C_{3-10}$ alkynyl group may be, for example, a 2-propynyl or 2-octynyl group.

It will be appreciated that the carbon atom at the 3-position of the tetrahydrocarbazolone ring is asymmetric and may exist in the R- or S- configuration. The present invention encompasses both the individual isomeric forms of the compounds of formula (I) and all mixtures, including racemic mixtures, thereof.

Suitable physiologically acceptable salts of the indoles of general formula (I) include acid addition salts formed with organic or inorganic acids for example, hydrochlorides, hydrobromides, sulphates, phosphates, citrates, fumarates and maleates. The solvates may, for example, be hydrates.

A preferred class of compounds represented by the general formula (I) is that wherein $R^1$ represents a hydrogen atom or a $C_{1-6}$ alkyl, $C_{3-6}$ cycloalkyl or $C_{3-6}$ alkenyl group.

Another preferred class of compounds represented by the general formula (I) is that wherein one of the groups represented by $R^2$, $R^3$ and $R^4$ represents a $C_{1-3}$ alkyl, $C_{3-6}$ cycloalkyl or $C_{3-6}$ alkenyl group and each of the other two groups, which may be the same or different, represents a hydrogen atom or a $C_{1-3}$ alkyl group.

A further preferred class of compounds represented by the general formula (I) is that wherein $R^1$ represents a hydrogen atom or a $C_{1-6}$ alkyl, $C_{5-6}$ cycloalkyl or $C_{3-4}$ alkenyl group, and either $R^2$ represents a hydrogen atom and $R^3$ and/or $R^4$ represents a $C_{1-3}$ alkyl group or $R^2$ represents a $C_{1-3}$ alkyl group and both $R^3$ and $R^4$ represent hydrogen atoms.

A particularly preferred class of compounds according to the invention is that represented by the formula (Ia):

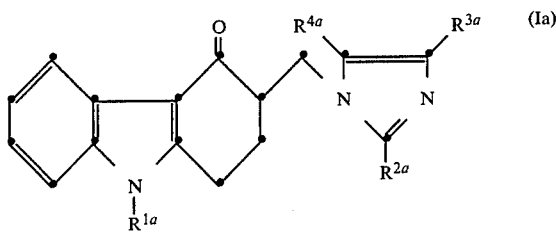

(wherein $R^{1a}$ represents a hydrogen atom or a methyl, ethyl, propyl, prop-2yl, prop-2-enyl or cyclopentyl group; $R^{3a}$ represents a hydrogen atom; and either $R^{2a}$ represents a methyl, ethyl, propyl or prop-2yl group and $R^{4a}$ represents a hydrogen atom or $R^{2a}$ represents a hydrogen atom and $R^{4a}$ represents a methyl or ethyl group) and physiologically acceptable salts and solvates (e.g. hydrates) thereof.

Preferred compounds are:
1,2,3,9-tetrahydro-3-[(2-methyl-1H-imidazol-1-yl)methyl]-9-(prop-2-enyl)-4H-carbazol-4-one;
9-cyclopentyl-1,2,3,9-tetrahydro-3-[(2-methyl-1H-imidazol-1-yl)methyl]-4H-carbazol-4-one; and
1,2,3,9-tetrahydro-3-[2-methyl-1H-imidazol-1-yl)methyl]-9-(prop-2-yl)-4H-carbazol-4-one
and their physiologically acceptable salts and solvates.

A particularly preferred compound is 1,2,3,9-tetrahydro-9-methyl-3-[(2-methyl-1H-imidazol-1-yl)methyl]-4H-carbazol-4-one which may be represented by the formula (Ib):

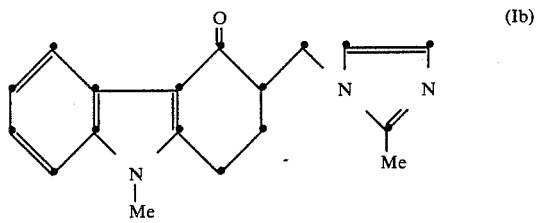

and the physiologically acceptable salts and solvates (e.g. hydrates) thereof. A preferred form of this compound is the hydrochloride dihydrate.

It will be appreciated that the invention extends to other physiologically acceptable equivalents of the compounds according to the invention, i.e. physiologically acceptable compounds which are converted in vivo into the parent compound of formula (I).

Compounds of the invention are potent and selective antagonists of 5HT-induced responses of the rat isolated vagus nerve preparation and thus act as potent and selective antagonists of the 'neuronal' 5HT receptor type located on primary afferent nerves.

Compounds of the invention are of use as analgesics, for example in the alleviation of pain associated with migraine, headache and many other forms of pain for which 5HT is the endogenous mediator.

Experiments in animals have shown that compounds of the invention are also of use in the treatment of schizophrenia and other psychotic disorders. As indicated herein above 5HT occurs widely in the neuronal pathways in the central nervous system and disturbance of these 5HT containing pathways is known to alter may other behavioural syndromes such as mood, appetite and memory. Since 'neuronal' 5HT receptors of the same type as those present on primary afferent terminals are also present in the central nervous system the compounds of the invention may also be useful in the treatment of conditions such as anxiety, obesity and mania.

In particular, compounds of formula (Ia) as previously defined have been found to be highly selective and extremely potent in their action. They are well absorbed from the gastro-intestinal tract and are suitable for oral or rectal administration. The compounds of formula (Ia) do not prolong sleeping time in the pentobarbitone anaesthetised mouse indicating that there is no undesireable interaction with drug metabolising enzymes. Indeed they exhibit no effects on normal behaviour, are non-toxic and exhibit no undesirable effects in mice at doses up to 1 mg/kg intravenously.

As well as exhibiting the outstanding properties of the compounds of formula (Ia), the compound of formula (Ib) when administered to humans showed no untoward effects.

According to another aspect, the invention provides a method of treatment of a human or animal subject suffering from a condition caused by a disturbance of 'neuronal' 5HT function. Thus, for example, the invention provides a method of treatment of a human subject suffering from migraine pain or a psychotic disorder such as schizophrenia.

Accordingly, the invention also provides a pharmaceutical composition which comprises a least one compound selected from 3-imidazolylmethyltetrahydrocarbazolone derivatives of the general formula (I), their physiologically acceptable salts and solvates, e.g. hydrates, adapted for use in human or veterinary medicine, and formulated for administration by any convenient route.

Such compositions may be formulated in conventional manner using one or more physiologically acceptable carriers or excipients.

Thus the compounds of the invention may be formulated for oral, buccal, parenteral or rectal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcelluslose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as supending agents (e.g. sorbitol syrup, cellulose derivatives or hydrogenated edible fats); emulsifying agents (e.g. lecithin or acacia); non-aqueous vehicles (e.g. almond oil, oily esters, ehtyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by injection. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as a depot preparation. Such long acting formulations may be adminsitered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

A proposed dose of the compounds of the invention for administration in man (of approximately 70 kg body wight) is 0.5 to 20 mg, preferably 0.1 to 10 mg of the active ingredient per unit dose which could be administered, for example, 1 to 4 times per day. The dose will depend on the route of administration and the body weight of the patient. It will be appreciated that it may be necessary to make routine variations to the dosage depending on the age and weight of the patient as well as the severity of the condition to be treated.

For oral administration a unit dose will preferably contain from 0.5 to 10 mg of the active ingredient. A unit dose for parenteral administration will preferably contain 0.1 to 10 mg of the active ingredient.

Aerosol formulations are preferably arranged so that each metered dose or 'puff' delivered from a pressurised aerosol contains 0.2 mg, of a compound of the invention, and, each dose administered via capsules and cartridges in an insufflator or an inhaler contains 0.2 to 20 mg of a compound of the invention. The overall daily dose by inhalation will be within the range 0.4 to 80 mg. Administration may be several times daily, for example from 2 to 8 times, giving for example 1, 2 or 3 doses each time.

The compunds of the invention may, if desired, be administered in combination with one or more other therapeutic agents, such as anti-nauseants.

According to another aspect of the invention, compounds of general formula (I) and physiologically acceptable salts or solvates or physiologically acceptable equivalents thereof may be prepared by the general methods outlined hereinafter.

According to a first general process (A), a compound of general formula (I) or a physiologically acceptable salt or solvate or a physiologically acceptable equivalent thereof may be prepared by reacting a compound of general formula (II):

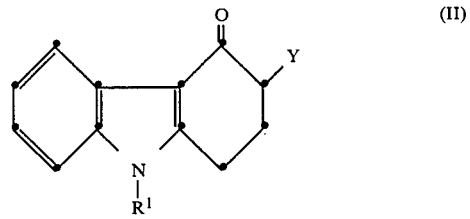

(wherein $R^1$ is as defined previously and Y represents a reactive substituent) or a protected derivative thereof with an imidazole of general formula (III):

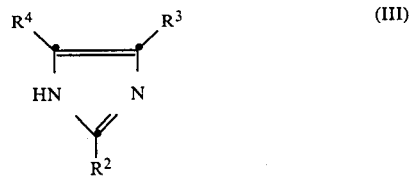

(wherein $R^2$, $R^3$ and $R^4$ are as defined previously) or a salt thereof.

Examples of compounds of formula (II) employed as starting materials in the process (A) include compounds wherein Y represents a group selected from an alkenyl group=$CH_2$ or a group of formula $Ch_2Z$ where Z represents a readily displaceable atom or group such as a halogen atom, e.g. chlorine or bromine; an acyloxy group such as acetoxy, trifluoromethanesulphonyloxy, p-toluene sulphonyloxy or methanesulphonyloxy; a group $-N^+R^5R^6R^7X^-$, where $R^5$, $R^6$ and $R^7$, which may be the same or different each represents lower alkyl e.g. methyl, aryl e.g. phenyl or aralkyl e.g. benzyl, or $R^5$ and $R^6$ together with the nitrogen atom to which they are attached may form a 5- to 6-membered ring e.g.

a pyrrolidine ring, and X represents an anion such as a halide ion e.g. chloride, bromide or iodide; or a group —NR$^5$R$^6$ where R$^5$ and R$^6$ are as defined above, for example —N(CH$_3$)$_2$.

When Y represents the group =CH$_2$, the process may conveniently be carried out in a suitable solvent, examples of which include water; esters, e.g. ethyl acetate; ketones, e.g. acetone; or methylisobutylketone; amides, e.g. dimethylformamide; alcohols, e.g. ethanol; and ethers e.g. dioxan or tetrahydrofuran; or mixtures thereof. The process may be effected at a temperature of, for example, 20° to 100° C.

When Y represents the group CH$_2$Z, where Z is a halogen atom or an acyloxy group, the process may conveniently be carried out in a suitable solvent such as an amide, e.g. dimethylformamide; and alcohol, e.g. methanol or industrial methylated spirit; or a haloalkane, e.g. dichloromethane, and at a temperature of from −10° to 150° C., e.g. +20° to +100 ° C.

The reaction of a compound of formula (II) where Y represents the group CH$_2$Z where Z is the group —N$^+$R$^5$R$^6$R$^7$X$^-$, may conveniently be carried out in a suitable solvent such as water, an amide, e.g. dimethylformamide; a ketone, e.g. acetone; or an ether, e.g. dioxan, and at a temperature of from 20° to 150° C.

The reaction including a compound of formula (II) where Y represents the group —CH$_2$Z, where Z is the group —NR$^5$R$^6$, may conveniently be carried out in a suitable solvent such as water or an alcohol, e.g. methanol, or mixtures thereof, and at a temperature of from 20° to 150° C.

According to another general process (B) a compound of formula (I) may be prepared by oxidising a compound of formula (IV):

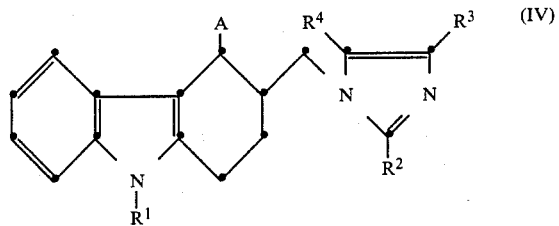

(wherein A represents a hydrogen atom or a hydroxyl group and R$^1$, R$^2$, R$^3$ and R$^4$ are as previously defined) or a salt or a protected derivative thereof.

The oxidation process may be effected using conventional methods and the reagents and reaction conditions should be chosen such that they do not cause oxidation of the indole group. Thus, the oxidation process is preferably effected using a mild oxidising agent.

When oxidising a compound of formula (IV) in which A represents a hydrogen atom, suitable oxidising agents include quinones in the presence of water, e.g. 2,3-dichloro-5,6-dicyano-,1,4-benzoquinone or 2,3,5,6-tetrachloro-1,4-benzoquinone; selenium dioxide; a cerium (IV) oxidising reagent such as ceric ammonium nitrate or a chromium (VI) oxidising agent, e.g. a solution of chromic acid in acetone (for example Jones' reagent) or chromium trioxide in pyridine.

When oxidising a compound of formula (IV) in which A represents a hydroxyl group, suitable oxidising agents include quinones in the presence of water, e.g. 2,3-dichloro-5,6-dicyano-1,4-benzoquinone or 2,3,5,6-tetrachloro-1,4-benzoquinone; ketones, e.g. acetone, methylethylketone or cyclohexanone, in the presence of a base e.g. aluminium t-butoxide; a chromium (VI) oxidising agent, e.g. a solution of chromic acid in acetone (for example Jones reagent) or chromium trioxide in pyridine; an N-halosuccinimide, e.g. N-chlorosuccinimide or N-bromosuccinimide; a dialkylsulphoxide e.g. dimethylsulphoxide, in the presence of an activating agent such as N,N'-dicylohexylcarbodiimide or an acyl halide, e.g. oxalyl chloride or tosyl chloride; pyridine-sulphur trioxide complex; or a dehydrogenation catalyst such as copper chromite, zinc oxide, copper or silver.

Suitable solvents may be selected from ketones, e.g. acetone or butanone; ethers e.g. tetrahydrofuran or dioxan; amides, e.g. dimethylformamide; alcohols, e.g. methanol; hydrocarbons, e.g. benzene or toluene; halogenated hydrocarbons, e.g. dichloromethane; and water or mixtures thereof.

The process is conveniently effected at a temperature of −70° to +50° C. It will be understood that the choice of oxidising agent will affect the preferred reaction temperature.

According to another general process (C), a compound of formula (I) according to the invention or a salt or protected derivative thereof may be converted into another compound of formula (I) using conventional techniques. Such conventional techniques include alkylation, which may be effected at any position in a compound of formula (I) where one or more of R$^1$ and R$^2$ represents a hydrogen atom, and hydrogenation, which may, for example, be used to convert an alkenyl substituent into an alkyl substituent or a cycloalkenylalkyl group into a cycloalkylalkyl substitutent. The term "alkylation" includes the introduction of other groups such as cycloalkyl or alkenyl groups. Thus, for example, a compound of formula (I) in which R$^1$ represents a hydrogen atom may be converted into the corresponding compound in which R$^1$ represents a C$_{1-10}$ alkyl, C$_{3-7}$ cycloalkyl, C$_{3-6}$ alkenyl, C$_{3-7}$ cycloalkyl-(C$_{1-4}$) alkyl, C$_{3-10}$ alkynyl or phenyl-C$_{1-3}$ alkyl group.

The above alkylation reactions may be effected using the appropriate alkylating agent selected from compounds of formula R$^a$X$^a$ where R$^a$ represents a C$_{1-10}$ alkyl, C$_{3-7}$ cycloalkyl, C$_{3-6}$ alkenyl, C$_{3-7}$ cycloalkyl-(C$_{1-4}$) alkyl, C$_{3-10}$ alkynyl or phenyl-C$_{13}$ alkyl group, and X$^a$ represents a leaving group such as a halide or an acyloxy group as previously defined for Y, or a sulphate of formula (R$^a$)$_2$SO$_4$.

The alkylation reaction is conveniently carried out in an inert organic solvent such as an amide, e.g. dimethylformamide; an ether, e.g. tetrahydrofuran; or an aromatic hydrocarbon, e.g. toluene, preferably in the presence of a base. Suitable bases include, for example, alkali metal hydrides such as sodium hydride, alkali metal amides such as sodium amide, alkali metal carbonates such as sodium carbonate or an alkali metal alkoxide such as sodium or potassium methoxide, ethoxide or t-butoxide. The reaction may conveniently be effected at a temperature in the range −20° to +100° C., preferably 0° to 50° C.

Hydrogenation according to general process (C) may be effected using conventional procedures, for example by using hydrogen in the presence of a noble metal catalyst e.g. palladium, Raney nickel, platinum, platinum oxide or rhodium. The catalyst may be supported on for example charcoal or a homogeneous catalyst such as tris(triphenylphosphine) rhodium chloride may be used. The hydrogenation will generally be effected in a solvent such as an alcohol, e.g. ethanol; an amide, e.g. dimethylformamide; an ether, e.g. dioxan; or an ester, e.g. ethyl acetate, and at a temperature in the range −20° to 100° C., preferably 0° to 50° C.

It should be appreciated that in some of the above transformations it may be necessary or desirable to protect any sensitive groups in the compound to avoid undesirable side reactions. The protecting groups used in the preparation of compounds of formula (I) are desirably groups which may be readily split off at a suitable stage in the reaction sequence, conveniently at the last stage. For example, during any of the reaction sequences described above, it may be necessary to protect the keto group, for example, as ketal or a thioketal.

Compounds of general formula (I) may thus be prepared according to another general process (D), which comprises removal of any protecting groups from a protected form of a compound of formula (I). Deprotection may be effected using conventional techniques such as those described in 'Protective Groups in Organic Chemistry' Ed. J. F. W. McOmie (Plenum Press, 1973). Thus, a ketal such as an alkyleneketal group may be removed by treatment with a mineral acid such as hydrochloric acid. The thioketal group may be cleaved by treatment with a mercuric salt, e.g. mercuric chloride, in a suitable solvent, such as ethanol.

The compounds of formula (I) may be converted into their physiologically acceptable salts according to conventional methods. Thus, for example, the free base of general formula (I) may be treated with an appropriate acid, preferably with an equivalent amount in a suitable solvent (e.g. aqueous ethanol).

Physiologically acceptable equivalents of a compound of formula (I) may be prepared according to conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E. L. Eliel (McGraw Hill 1962) and 'Tables of Resolving Agents' by S. H. Wilen.

Examples of optically active resolving acids that may be used to form salts with the racemic compounds include the (R) and (S) forms of organic carboxylic and sulphonic acids such as tartaric acid, di-p-toluoyltartaric acid, camphorsulphonic acid and lactic acid. The resulting mixture of isomeric salts may be separated, for example, by fractional crystallisation, into the diastereoisomers and if desired, the required optically active isomer may be converted into the free base.

The methods indicated above for preparing the compounds of the invention can be used as the last main step in the preparative sequence. The same general methods can be used for the introduction of the desired groups at an intermediate stage in the stepwise formation of the required compound, and it will be appreciated that these general methods can be combined in different ways in such multi-stage processes. The sequence of the reactions in multi-stage processes should of course be chosen so that the reaction conditions used do not affect groups in the molecule which are desired in the final product.

The starting materials of formula (II) wherein Y represents $=CH_2$ may be prepared from compounds of formula (II) where Y represents the group $CH_2N^+R^5R^6R^7X^-$ by reaction with a base in a suitable solvent. Examples of bases include alkali metal hydroxides, e.g. potassium hydroxide or alkali metal carbonates or hydrogen carbonates e.g. sodium hydrogen carbonate.

The quaternary salts may be formed from the corresponding tertiary amine by reaction with an alkylating agent such as methyl iodide or dimethyl sulphate, if preferred in a suitable solvent, e.g. dimethylformamide. The tertiary amine may be prepared by reaction of a tetrahydrocarbazolone of general formula (V):

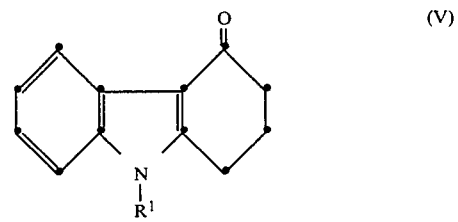

with formaldehyde and the corresponding secondary amine, if desired in a suitable solvent such as an alcohol, e.g. ethanol.

Compounds of general formula (V) may be prepared for example, by the method described by H. Iida et al. in J. Org. Chem. (1980) Vol 45, No. 15, pages 2938–2942.

The starting materials of general formula (II) where Y represents $-CH_2Z$ where Z is a halogen atom or an acyloxy group may be prepared from the corresponding hydroxymethyl derivative of general formula (VI):

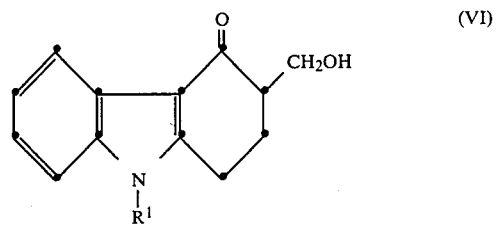

which may be obtained by reacting the tetrahydrocarbazolone of general formula (V) with formaldehyde, preferably in a suitable solvent such as an alcohol, e.g. ethanol, and preferably in the presence of a base.

Thus, the compounds where Z is a halogen atom may be obtained by reacting a compound of formula (VI) with a halogenating agent such as a phosphorus trihalide, e.g. phosphorus trichloride.

The compounds where Z is an acyloxy group may be prepared by reacting a compound of formula (VI) with an appropriate acylating agent such as an anhydride or a sulphonyl halide such as sulphonyl chloride.

Compounds of formula (II) where Y represents $-CH_2Z$ where Z is a halogen atom may also be prepared by reacting a compound of formula (II) where Y represents the group $=CH_2$ with the appropriate hydrogen halide, e.g. hydrogen chloride, conveniently in a suitable solvent such as an ether, e.g. diethyl ether.

Compounds of general formula (IV) may be prepared by reacting a compound of formula (VII):

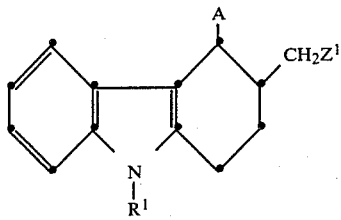

(VII)

(wherein R¹ and A are as defined previously and Z¹ is a readily displaceable atom or group such as a halogen atom, an acyloxy group or the group —N+R⁵R⁶R⁷X— as previously defined for Z¹) with an imidazole of formula (III) according to the method of process (A) described herein.

Compounds of formula (VII) may be prepared by reducing compounds of formula (II) using for example lithium aluminium hydride or sodium borohydride.

Compounds of formula (VII) wherein A represents a hydrogen atom may also be prepared by reacting a compound of formula (VII) wherein A represents a hydroxyl group with a tosyl halide (e.g. tosyl chloride) and then reducing the resulting tosylate with lithium aluminium hydride.

Compounds of formula (IV) are novel compounds, and as such provide a further feature of the invention.

The following examples illustrate the invention. Temperatures are in °C. where indicated, solutions were dried over Na₂SO₄ and solids were dried in vacuo over P₂O₅ at 50° overnight. Chromatography was carried out using the technique described by W. C. Still et al (J. Org. Chem., 1978, 43, 2923–2925), on kieselgel 9385.

The following abbreviations define the eluent used for column chromatography and t.l.c.

(A) Methylene chloride-ethanol-0.88 ammonia 100:10:1
(B) Methylene chloride-ethanol-0.88 ammonia 100:9:1
(C) Methylene chloride-ethanol-0.88 ammonia 200:10:1
(D) Methylene chloride-ethanol-0.88 ammonia 400:10:1

PREPARATION 1

2,3,4,9-Tetrahydro-N,N,N-trimethyl-4-oxo-1H-carbazole-3-methanaminium iodide

A solution of 3-[(dimethylamino)methyl]-1,2,3,9-tetrahydro-4H-carbazol-4-one (0.53 g) in iodomethane (15 ml) was heated under reflux for 5 h and evaporated to dryness, giving the title compound as a white solid (0.84 g) m.p. 202°–205°.

PREPARATION 2

2,3,4,9-Tetrahydro-N,N,N,9-tetramethyl-4-oxo-1H-carbazole-3-methanaminium iodide A suspension of 3-[(dimethylamino)methyl]-1,2,3,9-tetrahydro-9-methyl-4H-carbazol-4-one (3.80 g) in iodomethane (100 ml) was stirred at reflux for 57 h. The resulting suspension was concentrated in vacuo to give the title methanaminium iodide as a solid (5.72 g) m.p. 192°–195°.

PREPARATION 3

1,2,3,9-Tetrahydro-9-methyl-3-methylene-4H-carbazol-4-one

A solution of the product from Preparation 2 (5.0 g) in water (20 ml) was treated with 2N sodium carbonate (6.55 ml) and warmed at 35° for 45 mins. The resulting slurry was cooled to 0° and the solid was filtered off, washed with water and dried to give the title compound (2.8 g) m.p. 127°–129°.

PREPARATION 4

2,3,4,9-Tetrahydro-9-methyl-3-[(2-methyl-1H-imidazol-1-yl)methyl]-1H-carbazole maleate Sodium borohyrdide (90 mg) was added under nitrogen to a stirred solution of the product from Example 7 (500 mg) in a mixture of methanol (3 ml) and chloroform (3 ml). Stirring was continuted for 48 h (further sodium borohydride (250 mg) was added after 17.75 h and 42 h), and then the suspension was partitioned between 2N hydrochloric acid (15 ml) and chloroform (3×10 ml). The aqueous layer was basified with solid sodium carbonate, extracted with chloroform (3×10 ml), and the combined extracts washed with water (2×10 ml) and brine (10 ml), dried and concentrated in vacuo. Column chromatography of the residual foam (557 mg) eluting with a mixture of dichloromethane, ethanol and 0.88 aqueous ammonia (300:10:1) afforded a solid (200 mg). This material was dissolved in refluxing absolute ethanol (3 ml) and a solution of maleic acid (80 mg) in refluxing absolute ethanol (1 ml) was added. The hot solution was filtered, stirred, and diluted with dry ether (40 ml) to give the title compound (240 mg) m.p. 138.5°–140°

PREPARATION 5

2,3,4,9-Tetrahydro-9-methyl-3-[(2-methyl-1H-imidazol-1-yl)methyl]-1H-carbazol-4-ol The product from Example 7 (30.0 g) was added, under nitrogen, to a stirred suspension of lithium aluminium hydride (7.75 g) in dry tetrahydrofuran (750 ml). The mixture was stirred under reflux for 1 h and then cooled in ice. The suspension was cautiously diluted with aqueous tetrahydrofuran (15% H₂O; 100 ml) and water (100 ml), concentrated in vacuo and the residual solid extracted with dichloromethane (2×500 ml). The organic extracts were concentrated in vacuo and the residual solid (16.4 g) purified by short path column chromatography on silica (Kieselgel 60; Merck 7747; 500 g) eluted with a mixture of dichloromethane, ethanol and 0.88 aqueous ammonia (150:10:1) to give the title compound as a foam (13.4 g).

T.l.c. Silica, dichloromethane/ethanol/0.88 ammonia (150:10:1) Rf 0.34 and 0.36 (two pairs of diastereoisomers), detection u.v. and iodoplatinic acid.

N.m.r. δ[CDCl₃+CD₃OD (1 drop)] 1.6–2.3 and 2.6–3.0(5H,m), 2.32 and 2.40 (3H, s+s, Me in two different isomers), 3.32 (3H,s,NMe), 3.65–4.3(2H,m,CHCH₂N), 4.75–4.85(1H,m,CH—OH, 6.8–7.8 (CH,m,aromatic).

PREPARATION 6

1,2,3,9-Tetrahydro-3-[(2-methyl-1H-imidazol-1-yl)methyl]-4H-carbazol-4-one

A suspension of the product from Preparation 1 (6.6 g) and 2-methyl imidazole (17.0 g) in dry dimethylformamide (75 ml) was stirred at 100° under nitrogen for 17.25 h then cooled in ice to deposit a solid. This material was purified by washing successively with dimethylformamide (2×7 ml) and dry ether (3×15 ml) followed by column chromatography (A) to give the title compound (1.6 g) m.p. 235°–238° dec.

which was filtered whilst warm. The filtrate was then diluted with dry ether to deposit a solid (0.6 g) which was recrystallised from absolute ethanol to give the title compound as a solid (0.27 g) m.p. 186°–187°.

Analysis—Found: C,61.9;H,6.4;N,11.8. $C_{18}H_{19}N_3O.HCl.H_2O$ requires C,62.3;H,6.1;N,12.1%.

The following compounds were prepared by a similar procedure as detailed in Table I:

TABLE I

| Ex. No. | Formula I R$^1$ | R$^2$ | R$^3$ | R$^4$ | Wt S.M. (g) | Wt of appropriate Imidazole (g) | Vol. Solvent (ml) | Salt Formed | Wt. Product (g) | m.p. | Molecular Formula | Analysis (%) Found C | H | N | Requires C | H | N |
|---|---|---|---|---|---|---|---|---|---|---|---|---|---|---|---|---|---|
| 1b | CH$_3$ | H | H | H | 2.00 | 4.10 | 30 | HCl | 0.78 | 199.5–200.5° | $C_{17}H_{17}N_3O.HCl.0.8H_2O$ | 62.05 | 5.5 | 12.7 | 61.8 | 5.9 | 12.7 |
| 1c | CH$_3$ | H | CH$_3$ | CH$_3$ | 0.8 | 0.6 | 5 | Maleate | 0.50 | 151–152 | $C_{19}H_{21}N_3O.C_4H_4O_4.0.2H_2O$ | 64.6 | 6.0 | 9.8 | 64.7 | 6.0 | 9.8 |
| 1d | CH$_3$ | $^i$Pr | H | H | 3.2 | 2.9 | 40 | HCl | 1.0 | 178–182° | $C_{20}H_{23}N_3O.HCl.0.5H_2O$ | 64.9 | 6.9 | 11.2 | 65.5 | 6.9 | 11.45 |
| 1e* | Me | H | CH$_2$Ph | H | 0.8 | 1.2 | 5 | HCl | 0.25 | 130–135° | $C_{24}H_{23}N_3O.HCl.0.5H_2O$ | 69.1 | 6.1 | 9.9 | 69.5 | 6.1 | 10.1 |
| 1f* | Me | H | H | CH$_2$Ph | | | | — | 0.05 | 170–174° | $C_{24}H_{23}N_3O.1.5 H_2O$ | 72.8 | 6.2 | 10.5 | 72.7 | 6.6 | 10.6 |
| 1g* | Me | ζ | H | H | 1.0 | 1.6 | 30 | HCl | 0.3 | 150–155° | $C_{23}H_{27}N_3O.HCl.0.3H_2O$ | 68.5 | 7.55 | 10.4 | 68.4 | 7.15 | 10.4 |

*2,3,4,9-Tetrahydro-9,N,N,N—tetramethyl-4-oxo-1H—carbazol-3-methanaminium methosulphate used as starting material.
In the Table, ζ represents cyclohexyl.
Note 1
Compounds 1e and 1f were prepared in the same experiment and the isomers separated by short path chromatography (D. F. Taber, J. Org. Chem., 1982, 47, 1351) eluting with dichloromethane/ethanol/ 0.88 ammonia (300:10:1). The following $^1$H n.m.r. data was obtained.

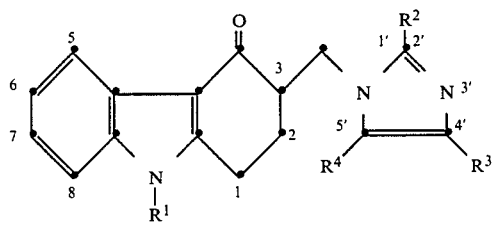

$^1$H NMR SPECTRA (obtained at 250 MHz)
Selected Proton Chemical Shifts (δ ppm) and multiplicities

| | | Carbazolone Protons | | | Imidazole Protons | |
|---|---|---|---|---|---|---|
| | Solvent | Aromatic H-5,6,7,8 | Aliphatic CH$_2$-1 and CH$_2$-2 H-3 | Imidazolyl Methylene Protons | H-2' | H-4' and/or H-5' |
| 1e | d$_6$-DMSO | 7.2–8.05 | 2.91–3.25 1.75–2.3 | 4.47(dd) and 4.64(dd) | 9.20s | 7.55s |
| 1f | CDCl$_3$ + DMSO | 7.15–8.05 | 2.6–3.05 1.75–2.1 | 4.02(dd) and 4.63(dd) | 8.17s | 6.93s |
| 1g | d$_6$-DMSO | 7.2–8.05 | inter alia 2.9–3.3  1.6–2.2 | 4.42(dd) and 4.73(dd) | — | 7.61d and 7.70 | d = doublet
dd = doublet of doublets
s = singlet

EXAMPLE 1a 1,2,3,9-Tetrahydro-9-methyl-3-[(2-methyl-1H-imidazol-1-yl)methyl]-4H-carbazol-4-one hydrochloride A solution of the product of Preparation 2 (2.0 g) and 2-methylimidazole (5.0 g) in dry dimethylformamide (30 ml) was stirred, under nitrogen, at 95° for 16.75 h and then allowed to cool. The solid that crystallised was filtered off, washed with ice-cold, dry dimethylformamide (3×2 ml) and dry ether (2×10 ml) and then dried. The resulting solid (0.60 g) was suspended in a mixture of absolute ethanol (30 ml) and ethanolic hydrogen chloride (1 ml), and warmed gently to obtain a solution,

EXAMPLE 2

1,2,3,9-Tetrahydro-9-methyl-3-[(2-methyl-1H-imidazol-1-yl)methyl]-4H-carbazol-4-one maleate 1,2,3,9-Tetrahydro-9-methyl-3-[(2-methylimidazol-1-yl)methyl-4H-carbazol-4-one (300 mg) was suspended in hot ethanol (5 ml) and treated with maleic acid (116 mg). The solution was cooled and the white crystalline solid was filtered off and dried to give the title compound (300 mg) m.p. 132.3°.

EXAMPLE 3a

1,2,3,9-Tetrahydro-3-(1H-imidazol-1-ylmethyl)-4H-carbazol-4-one

A solution of the product of Preparation 1 (0.84 g) and imidazole (0.90 g) in dimethylformamide (25 ml) was heated at 105° for 6 h, cooled, added to water (200 ml) and extracted six times with ethyl acetate. The combined extract was washed, dried and evaporated to give a solid which was purified on a silica column (Merck 7734) eluting with ethyl acetate/methanol (4:1). Recrystallisation twice from ethyl acetate/methanol gave the title compound (0.095 g) as a crystalline solid m.p. 220°–222°.

T.l.c. Silica, dichloromethane/ethanol/0.88 ammonia (100:8:1) Rf 0.33, detection u.v. and iodoplatinic acid.

The following compounds were prepared by a similar procedure as detailed in Table II. Salt formation was carried out as described in Example 2.

EXAMPLE 4

1,2,3,9-Tetrahydro-9-methyl-3-[(2-methyl-1H-imidazol-1-yl)methyl]-4H-carbazol-4-one A solution of 1,2,3,9-tetrahydro-3-[(2-methyl-1H-imidazol-1-yl)methyl]-4H-carbazol-4-one (1.0 g) in dry dimethylformamide (10 ml) was added dropwise under nitrogen to a stirred, ice-cooled suspension of sodium hydride (80% in oil; 0.11 g) in dry dimethylformamide (5 ml). After 0.5 h dimethylsulphate (0.34 ml) was added, and the solution stirred at room temperature for 4 h. The resultant solid was filtered off, washed with ice-cold dry dimethylformamide (2×5 ml) and dry ether (3×15 ml) and dried to give the title compound as a solid (0.25 g) m.p. 223°–224° (dec).

T.l.c. Silica, chloroform/methanol (93:7) Rf 0.27 detection u.v. and iodoplatinic acid, identical to the product from Example 1a.

The following compounds were prepared by a similar procedure using the appropriate alkylating agent as detailed in Table III.

TABLE II

| Ex. No. | Formula (I) | | | | Wt S.M. (g) | Wt of appropriate Imidazole (g) | Vol Solvent (ml) | Rection Time/Temp. (h/°C.) | Salt Formed | Wt. Product (g) | m.p. |
|---|---|---|---|---|---|---|---|---|---|---|---|
| | $R^1$ | $R^2$ | $R^3$ | $R^4$ | | | | | | | |
| 3b | H | CH$_3$ | H | H | 6.60 | 17.00 | 75 | 17.25/100 | Maleate | 0.40 | 155–156° |
| 3c | H | CH$_2$CH$_3$ | H | H | 7.00 | 10.50 | 75 | 18/85 | Maleate | 0.48 | 154.5–156° |
| 3d | H | CH$_2$Ph | H | H | 3.00 | 3.10 | 25 | 24/100 | Maleate | 0.61 | 100.5–102° |
| 3e | H | H | CH$_3$ | H | 1.00 | 2.2 | 5 | 18/95 | Maleate | 0.16 | 144–145.5° |
| 3f | H | H | H | CH$_3$ | | | | | Maleate | 0.09 | 143–144° |
| 3g | H | γ | H | H | 1.80 | 1.0 | 20 | 20/100 | HCl | 0.11 | 142–146° |

<sup></sup>

'H NMR SPECTRA (obtained at 250 MHz in d$_6$-DMSO)
Selected Proton Chemical Shifts (δ ppm) and multiplicities

| | Carbazolone | | | Imidazole | |
|---|---|---|---|---|---|
| Ex. No. | Aromatic H-5,6,7,8 | Aliphatic CH$_2$-1 and CH$_2$-2 | H-3 | Imidazolyl Methylene | H-2' | H-4' and/or H-5' |
| 3b | 7.1–8.05 | 3.0–3.25 | 1.9–2.2 | 4.29(dd) and 4.69(dd) | — | 7.57d and 7.67d |
| 3c | 7.15–8.05 | 3.0–3.25 | 1.9–2.2 | 4.32(dd) and 4.72(dd) | — | 7.61d and 7.69d |
| 3d | 7.15–8.05 | 2.85–3.1 | 1.8–2.05 | 4.28(dd) and 4.71(dd) | — | 7.59d and 7.71d |
| 3e | 7.15–8.05 | 3.0–3.20 | 1.75–2.25 | 4.48(dd) and 4.62(dd) | 8.97s | 7.46s |
| 3f | 7.15–8.05 | 3.0–3.20 | 1.90–2.20 | 4.29(dd) and 4.74(dd) | 8.93s | 7.41s |
| 3g | 7.1–8.0 | 2.9–3.2 | 1.75–2.1 | 6.32(dd) and 6.70(dd) | — | 7.75d and 7.83d |

NOTE 1
Compounds 3e and 3f were prepared in the same experiment and the isomers separated by preparative h.p.l.c. on Zorbax-Sil eluting with hexane/ethyl acetate/ethanol/0.88 ammonia (400:100:100:0.6).
In the Table, the positions of the protons are numbered with reference to the formula below,

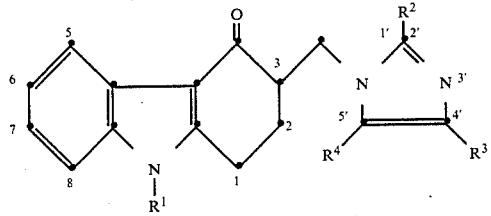

The symbols in Table II have the following meanings
d = doublet, dd = doublet of doublets, s = singlet
γ represents the group 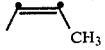

TABLE III

| Example No. | Alkylating Agent | R² | R³ | R⁴ | Reaction Time (h) at RT | Salt Formed | Wt. Product (g) | m.p. |
|---|---|---|---|---|---|---|---|---|
| 4b | Me₂SO₄ | CH₂CH₃ | H | H | 0.5 | HCl | 0.13 | 211–212° |
| 4c | Me₂SO₄ | CH₂Ph | H | H | 4 | Maleate | 0.32 | 143–145° |
| 4d | Et₂SO₄ | CH₃ | H | H | 6.5 | Maleate | 0.67 | 159–160° |
| 4e | PhCH₂Br | CH₃ | H | H | 5.75 | Maleate | 1.00 | 150–151.5° |
| 4f | CH₃(CH₂)₅I | CH₃ | H | H | 7.25 | Maleate | 1.16 | 118–119° |
| 4g | Ph(CH₂)₃Br | CH₃ | H | H | 5.75 | Maleate | 0.84 | 95–96.5° |
| 4h | CH₃(CH₂)₉OSO₂-C₆H₄-CH₃ | CH₃ | H | H | 4 (at 50°) | Oxolate | 0.14 | 50–51° |
| 4i | Et₂CHOSO₂-C₆H₄-CH₃ | CH₃ | H | H | 14h (at 40° C.) | HCl | 0.12 | 131–133° |

| Example No. | Molecular Formula | Analysis (%) Found C | H | N | Requires C | H | N |
|---|---|---|---|---|---|---|---|
| 4b | C₁₉H₂₁N₃O.HCl.0.5H₂O | 64.7 | 6.5 | 11.0 | 64.7 | 6.6 | 11.9 |
| 4c | C₂₄H₂₃N₃O.C₄H₄O₄ | 69.35 | 5.5 | 8.5 | 69.3 | 5.6 | 8.65 |
| 4d | C₁₉H₂₁N₃O.C₄H₄O₄ | 65.15 | 6.1 | 9.85 | 65.25 | 5.95 | 9.9 |
| 4e | C₂₄H₂₃N₃O.C₄H₄O₄ | 69.1 | 5.65 | 8.55 | 69.3 | 5.6 | 8.65 |
| 4f | C₂₃H₂₉N₃O.C₄H₄O₄ | 67.4 | 6.9 | 8.7 | 67.6 | 6.9 | 8.8 |
| 4g | C₂₆H₂₇N₃O.C₄H₄O₄.0.2H₂O | 69.5 | 5.9 | 8.0 | 69.7 | 6.1 | 8.1 |
| 4h | C₂₇H₃₇N₃O.C₂H₂O₄.0.3H₂O | 66.7 | 7.8 | 7.8 | 66.6 | 7.8 | 8.0 |
| 4i | C₂₂H₂₇N₃O.HCl.1.1H₂O | 65.8 | 7.9 | 10.3 | 65.4 | 7.5 | 10.4 |

Note 1
The following ¹H n.m.r. data was obtained.

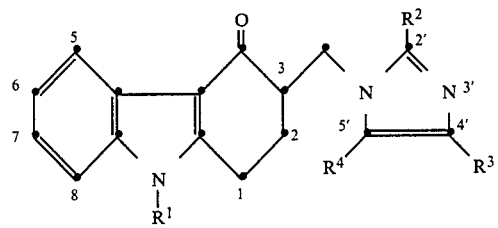

¹H NMR SPECTRA (obtained at 250 MHz)
Selected Proton Chemical Shifts (δ ppm) and multiplicities

| | | Carvazolone Protons | | Imidazolyl | Imidazole Protons | |
|---|---|---|---|---|---|---|
| | | Aromatic | Aliphatic | Methylene | | H-4′ and/or |
| | Solvent | H-5,6,7,8 | CH₂-1 and CH₂-2 H-3 | Protons | H-2′ | H-5′ |
| 4g | d₆-DMSO | 7.15–8.1 | 2.9–3.2    1.9–2.2 | 6.29(dd) and 6.68(dd) | — | 7.55d and 7.65d |
| 4h | d₆-DMSO | 7.2–8.1 | 2.9–3.3    1.8–2.2 | 6.26(dd) and 6.65(dd) | — | 7.42d and 7.57d | d = doublet
dd = doublet of doublets

EXAMPLE 5

9-Cyclopentyl-1,2,3,9-tetrahydro-3-[(2-methyl-1H-imidazol-1-yl)methyl]-4H-carbazol-4-one maleate A solution of 1,2,3,9-tetrahydro-3-[(2-methyl-1H-imidazol-1-yl)methyl]-4H-carbazol-4-one (1.20 g) in dry dimethylformamide (9 ml) was added to a stirred, ice-cooled, suspension of sodium hydride (80% in oil; 0.14 g) in dry dimethylformamide (2 ml) under nitrogen, and stirring continued for 0.25 h. Bromocyclopentane (0.51 ml) was added and the stirred solution heated at 100° for 18.5 h. The solution was allowed to cool and then partitioned between water (100 ml) and ethyl acetate (3×70 ml). The combined organic extracts were washed with 2N sodium carbonate (2×50 ml), water (2×50 ml) and brine (50 ml), dried, evaporated to dryness and purified by chromatography eluting with a mixture of dichloromethane, ethanol, 0.88 ammonia (150:10:1) to give an oil (0.27 g). This oil was dissolved in refluxing absolute ethanol (7 ml) and a solution of maleic acid (0.10 g) in refluxing absolute ethanol (0.5 ml) was added. The hot solution was filtered, stirred and diluted with dry ether (20 ml). The resultant yellow gum was washed with dry ether (7×25 ml), and the combined mother-liquors and washings left to stand. The solid that crystallised from the solution was filtered off, washed with dry ether (3×5 ml) and dried to give the title salt as a white crystalline solid (0.058 g), m.p. 104.5°–106°

Analysis—Found: C,65.95;H,6.4;N,8.6. $C_{22}H_{25}N_3O.C_4H_4O_4..6H_2O$ requires C,65.8;H,6.4;N,8.9%.

EXAMPLE 6

1,2,3,9-Tetrahydro-3-[(2-methyl-1H-imidazol-1-yl)methyl]-9-(2-propenyl)-4H-carbazol-4-one maleate A solution of 1,2,3,9-tetrahydro-3-[(2-methyl-1H-imidazol-1-yl)methyl]-4H-carbazol-4-one (1.0 g) in dry dimethylformamide (6 ml) was added to a stirred, ice-cooled suspension of sodium hydride (80% in oil; 0.12 g) in dry dimethylformamide (2 ml). After 0.25 h allyl bromide was added, the solution stirred at 0° for 0.25 h, and at room temperature for 20 h before partitioning between water (75 ml) and ethyl acetate (3×50 ml). The combined organic extracts were washed with water (2×50 ml), brine (50 ml), dried, and concentrated in vacuo and purified by chromatography eluting with a mixture of dichloromethane, ethanol, and 0.88 aqueous ammonia (200:10:1) to afford a solid (0.43 g). This solid was dissolved in refluxing absolute ethanol (2 ml) and a solution of maleic acid (0.18 g) in refluxing absolute ethanol (1 ml) was added. The hot solution was filtered, diluted with dry ether (4 ml) and the crystallised solid was filtered off, washed with dry ether (3×5 ml) and dried to give the title compound as a white solid (0.48 g), m.p. 150.5°–151°

Analysis—Found: C,66.3;H,5.75;N,9.6. $C_{20}H_{21}N_3O.C_4H_4O_4$ requires C,66.2;H,5.8;N,9.65%.

EXAMPLE 7

1,2,3,9-Tetrahydro-9-methyl-3-[(2-methyl-1H-imidazol-1-yl)methyl]-4H-carbazol-4-one A solution of 3-[(dimethylamino)methyl]-1,2,3,9-tetrahydro-9-methyl-4H-carbazol-4-one hydrochloride (1.7 g) in water (17 ml) was treated with 2-methylimidazole (1.4 g) and then heated under reflux for 20 h. The cooled mixture was filtered and the residue washed with water (3×15 ml) to give crude product (1.7 g) m.p. 221°–221.5°. This material was recrystallised from methanol to give the title compound (1.4 g) m.p. 231°–232°, identical by t.l.c. with product from Example 4.

EXAMPLE 8

1,2,3,9-Tetrahydro-9-methyl-3-[(2-methyl-1H-imidazol-1-yl)methyl]-4H-carbazol-4-one A suspension of the product from Preparation 3 (0.5 g) and 2-methylimidazole (0.4 g) in water (5 ml) was heated under reflux for 20 h. The cooled reaction mixture was filtered and the residue washed with water (3×10 ml), dried and recrystallized from methanol (18 ml) to give the title compound (0.3 g) m.p. 232°–234° (dec), identical by t.l.c. with the product from Example 4.

EXAMPLE 9

1,2,3,9-Tetrahydro-9-(1-methylethyl)-3-[(2-methyl-1H-imidazol-1-yl)methyl]-4H-carbazol-4-one hydrochloride Sodium hydride (80% dispersion in oil 0.208 g) was added to a stirred solution of 1,2,3,9-tetrahydro-3-[(2-methyl-1H-imidazol-1-yl)methyl]-4H-carbazol-4-one (1.93 g) at 0° C. in DMF (35 ml) and the resultant suspension stirred at 0° C. for 0.25 h. 2-Bromopropane (0.78 ml) was then added and stirring continued at room temperature overnight, followed by 4 h at 40° C.

The reaction mixture was partitioned between sodium carbonate (2N; 200 ml) and ethyl acetate (2×150 ml). The combined organic extracts were washed with water (3×75 ml), dried, and evaporated in vacuo and the product purified by chromatography eluting with dichloromethane:ethanol:ammonia (100:8:1) to give an oil. This oil was dissolved in ethanol (3 ml), acidified with ethereal hydrogen chloride and diluted with dry ether to deposit the title compound as a white solid (0.13 g) m.p. 230°–232°.

Analysis—Found: C,65.3;H,6.6;N,11.1%. $C_{20}H_{23}N_3O.HCl.O.5H_2O$ requires C,65.4;H,6.9;N,11.45%.

EXAMPLE 10

1,2,3,9-Tetrahydro-9-methyl-3-[(2-methyl-1H-imidazol-1-yl)methyl]-4H-carbazol-4-one hydrochloride dihydrate 1,2,3,9-Tetrahydro-9-methyl-3-[(2-methyl-1H-imidazol-1-yl)methyl]-4H-carbazol-4-one (18.3 g) in a hot mixture of isopropanol (98 ml) and water (18.3 ml) was treated with concentrated hydrochloric acid (6.25 ml). The hot mixture was filtered and the filtrate diluted with isopropanol (90 ml) and stirred at room temperature for 17 h, cooled to 2° and the solid filtered off (21.6 g). A sample (6 g) was recrystallized from a mixture of water (6 ml) and isopropanol (10 ml) to give the title compound as a white crystalline solid (6 g) m.p. 178.5°–179.5°.

Analysis—Found: C,59.45;H,6.45;N,11.5. $C_{18}H_{19}N_3O.HCl.2H_2O$ requires C,59.1; H, 6.6; N,11.5%. Water assay—Found: 10.23%. $C_{18}H_{19}N_3O.HCl.2H_2O$ requires 9.85%.

EXAMPLE 11

1,2,3,9-Tetrahydro-3-[(2-methyl-1H-imidazol-1-yl)methyl]-9-phenyl-4H-carbazol-4-one maleate (i) 3-[(Dimethylamino)methyl]-1,2,3,9-tetrahydro-9-phenyl-4H-carbazol-4-one hydrochloride A solution of 1,2,3,9-tetrahydro-9-phenyl-4H-carbazol-4-one (3.90 g) dimethylamine hydrochloride (1.50 g) and paraformaldehyde (0.60 g) in glacial acetic acid was stirred at reflux under nitrogen for 42 h, allowed to cool and concentrated in vacuo. The residual brown gum was stirred with water (50 ml), ethyl acetate (50 ml) and brine (20 ml) for 0.25 h, and the resultant solid filtered off, washed with dry ether (4×30 ml) and dried to give the title compound (4.2 g). A portion of this solid (1.0 g) was recrystallised twice from absolute ethanol (10 ml) to give the title compound as a fawn powder (0.39 g) m.p. 193°–194° (dec).

(ii)
1,2,3,9-Tetrahydro-3-[(2-methyl-1H-imidazol-1-yl)methyl]-9-phenyl-4H-carbazol-4-one maleate 2-Methyl-1H-imidazole (1.4 g) was added, under nitrogen, to a stirred suspension of 3-[(dimethylamino)methyl]-1,2,3,9-tetrahydro-9-phenyl-4H-carbazol-4-one hydrochloride (2.0 g) in water (20 ml). The mixture was heated at 90° for 43 h and the solvent decanted from the fawn solid. Chloroform was added to the solid, the suspension was filtered through hyflo, the filtrate dried and concentrated in vacuo.

Chromatography of the residual fawn foam (2.04 g) eluting with a mixture of dichloromethane, ethanol and 0.88 aqueous ammonia (200:10:1) afforded a white foam (1.1 g). A solution of this foam in ethanol (3 ml) was treated with maleic acid (0.4 g) in ethanol (1 ml) followed by dry ether (40 ml) and the resultant gum triturated with dry ether (2×40 ml) to afford the title compound as a cream solid (1.37 g), m.p. 165°–166° (dec).
Analysis—Found: C,68.65;N,5.5;N,8.7. $C_{23}H_{21}N_3O.C_4H_4O_4$ requires C,68.8; N,5.3; N,8.9%.

EXAMPLE 12

1,2,3,9-Tetrahydro-9-methyl-3-[(2-methyl-1H-imidazol-1-yl)methyl]-4H-carbazol-4-one phosphate (1:1)

1,2,3,9-Tetrahydro-9-methyl-3-[(2-methyl-1H-imidazol-1-yl)methyl]-4H-carbazol-4-one (0.61 g) was dissolved in a hot mixture of phosphoric acid (90%, 0.13 ml) and water (10 ml), filtered through Hyflo and allowed to crystallize to give the title compound (0.5 g) m.p. 225°
Analysis—Found: C,55.1;H,5.6;N,10.55. $C_{18}H_{19}H_3O.H_3PO_4$ requires C,55.2;H,5.7;N,10.7%.

EXAMPLE 13

1,2,3,9-Tetrahydro-9-methyl-3-[(2-methyl-1H-imidazol-1-yl)methyl]-4H-carbazol-4-one citrate (2:1)

1,2,3,9-Tetrahydro-9-methyl-3-[(2-methyl-1H-imidazol-1yl)methyl]-4H-carbazol-4-one (0.89 g) was dissolved in a hot solution of citric acid (0.58 g) in ethanol (20 ml) and allowed to crystallize. The resulting crystalline solid was recrystallized by dissolving in acetone/water (2:1, 2 ml) and diluting with acetone (20 ml) to give the title compound (0.6 g) m.p. 162°.

EXAMPLE 14

1,2,3,9-Tetrahydro-3-[(2-propyl-1H-imidazol-1-yl)methyl]-4H-carbazol-4-one hydrochloride Iodomethane (0.75 ml) was added to a stirred solution of 3-[(dimethyl amino)methyl]-1,2,3,9-tetrahydro-4H-carbazol-4-one (2.9 g) in dry DMF (30 ml) and the solution stirred at room temperature for 30 min. A solution of 2-propyl-1H-imidazole (2 g) in DMF (5 ml) was added, and the solution stirred at 100° C. for 2 days, cooled and partitioned between sodium carbonate (2N, 150 ml) and ethyl acetate (2×100 ml). The combined extracts were washed with water (100 ml), dried and evaporated in vacuo. The residue was purified by column chromatography eluting with dichloromethane:ethanol:ammonia (400:30:3) to give the free base as a solid (1.2 g). A sample (0.2 g) was dissolved in absolute ethanol (5 ml), acidified with ethereal hydrogen chloride and diluted with dry ether (ca 200 ml) to give an oil. On scratching, the oil crystallised to give a solid (0.15 g). The salt was crystallised from a mixture of methanol and isopropyl acetate to give the title compound (0.08 g) m.p. 206°208° C.
Analysis—Found: C,65.6;H,6.8;N,12.0. $C_{19}H_{21}N_3O.HCl$ 0.2H$_2$O requires C,65.7;H,6.5;N,12.1%.
N.m.r. δ(CD$_3$SOCD$_3$) 0.94(3H,t,CH$_3$), 1.77(2H, sextet, CH$_2$CH$_2$CH$_3$), 1.9–2.15 and 2.95–3.2 (7H,m) 4.32 and 4.71 (2H, ABX, CHCH$_2$N), 7.1–8.0(6H, aromatic).

EXAMPLE 15

1,2,3,9-Tetrahydro-3-[(2-propyl-1H-imidazol-1-yl)methyl]-4H-carbazol-4-one hydrochloride A solution of the product from Example 3g (0.03 g) in methanol (15 ml) was hydrogenated at room temperature and pressure over 10% palladium oxide on charcoal (50% aq. paste, 0.03 g) for 4h (H$_2$ uptake, 5 ml). The catalyst was filtered off, and the filtrate evaporated in vacuo to given an oil. Trituration with ether gave the title compound as a white solid (0.03 g) m.p. 199°–203° C.

this material was identified by t.l.c. and n.m.r. to the product from Example 14.

EXAMPLE 16

1,2,3,9-Tetrahydro-3-[(2-propyl-1H-imidazol-1yl)methyl]-4H-carbazol-4-one hydrochloride Sodium hydride (80% disp. in oil) was added, under nitrogen, to a stirred solution of the product from Example 14 (1.0 g) in dry DMF (20 ml) and the suspension stirred at room temperature for 30 min. 1-Bromopropane (0.35 ml) was added, and the solution stirred at 40° C. for 20 h. The solution was partitioned between sodium carbonate (2N, 150 ml) and ethyl acetate (2×100 ml). The combined extracts were washed with water (100 ml), dried and evaporated in vacuo to give an oil. The oil was purified by column chromatography eluting with dichloromethane:ethanol:ammonia (100:8:1) to give pure free base as an oil. The oil was dissolved in absolute ethanol (5 ml), acidified with ethereal hydrogen chloride, and diluted with dry ether (200 ml). The ether was decanted off the resulting oil and replaced with more dry ether (200 ml). On storage at 0° C. overnight the oil crystallised to give the title compound (0.53 g) m.p. 144°–147° C.
N.m.r. δ(CD$_3$SOCD$_3$) 0.90 and 0.93(6H,t+t, 2×Me), 1.65–2.2 and 2.9–3.25 (10H,m), 4.19(2H,t,CH$_2$CH$_2$N), 4.32 and 4.71(2H,e,uns/AB/ X,CH$_2$CH$_2$N), 7.15–8.1(6H,m,aromatic)
Analysis Found: C,66.6;H,7.7;N,10.0. $C_{22}H_{27}N_3O.HCl.07H_2O$ requires C,66.3;H,7.4;N,10.5%.

EXAMPLE 17

1,2,3,9-Tetrahydro-3-[(2-methyl-1H-imidazol-1-yl)methyl]-9-propyl-4H-carbazol-4-one maleate A solution of the product from Example 6 (0.86 g) in a mixture of absolute ethanol (20 ml) and dry dimethylformamide (5 ml) was hydrogenated at room temperature and pressure over 5% platinum on carbon [(0.1 g, pre-reduced in absolute ethanol (10 ml)] for 1 h. (H$_2$ uptake=70 ml). The catalyst was filtered off, washed with ethanol, and the filtrate concentrated in vacuo to ca 15 ml. The residual solution was stirred, diluted with water (50 ml) and the precipitated solid filtered off, washed with water (3×15 ml) and dried to give a powder (0.73 g).

This material was dissolved in refluxing absolute ethanol (7 ml), filtered, and a solution of maleic acid (0.25 g) in refluxing absolute ethanol (1 ml) was added. The stirred solution was diluted with dry ether (50 ml) to give the title compound (0.84 g), m.p. 150°–151°
Analysis—Found: C,65.8;H,6.1;N,9.3; $C_{20}H_{23}N_3O.C_4H_4O_4$ requires C,65.9;H,6.2;N,9.6%.

EXAMPLE 18

1,2,3,9-Tetrahydro-9-methyl-3-[(2-methyl-1H-imidazol-1-yl)methyl]-4H-carbazol-4-one (i) 3-(Chloromethyl)-1,2,3,9-tetrahydro-9-methyl-4H-carbazol-4-one Ethereal hydrogen chloride (3.0 ml) was added to a stirred, ice-cooled solution of the product from Preparation 3 (1.90 g) in chloroform (15 ml), and the resultant suspension was stirred in a sealed vessel at room temperature for 16.5 h, concentrated in vacuo and the residual solid (2.27 g) purified by column chromatography eluting with chloroform to give the title compound (1.75 g) m.p. 109°–110.5°. An attempt to crystallise a portion of this material from ethyl acetate resulted in partial decomposition.

(ii) 1,2,3,9-Tetrahydro-9-methyl-3-[(2-methyl-1H-imidazol-1-yl)methyl]-4H-carbazol-4-one A solution of 3-(chloromethyl)-1,2,3,9-tetrahydro-9-methyl-4H-carbazol-4-one (0.50 g) and 2-methyl-1H-imidazole (1.60 g) in dry DMF was stirred under nitrogen at 90° for 3.75 h, and then poured onto water (25 ml). The suspension was stirred for 1 h, and the solid filtered off, washed with water (3×20 ml) and dried in vacuo at 50°. Column chromatography of this solid (0.53 g) eluting with a mixture of dichloromethane, ethanol and 0.88 aqueous ammonia (150:10:1) afforded the title compound (0.45 g) m.p. 228°–229°. This material was identical to the product from Example 7 by t.l.c. and n.m.r.

EXAMPLE 19

1,2,3,9-Tetrahydro-9-methyl-3-[(2-methyl-1H-imidazol-1-yl)methyl]-4H-carbazol-4-one A solution of 2,3-dichloro-5,6-dicyano-1,4-benzoquinone (170 mg) in dry tetrahydrofuran (1.5 ml) was added dropwise under nitrogen to a stirred, ice-cooled suspension of the product from Preparation 4 (100 mg) in a mixture of tetrahydrofuran (3.5 ml) and water (0.4 ml). The resultant blue solution was stirred for 1.5 h, and then concentrated in vacuo. Column chromatography of the residual solid eluting with a mixture of dichloromethane, ethanol and 0.88 ammonia (150:10:1) afforded the title compound (45 mg) m.p. 227°–228.5°. This material was identical to the product from Example 7 by t.l.c. and n.m.r.

EXAMPLE 20

1,2,3,9-Tetrahydro-9-methyl-3-[(2-methyl-1H-imidazol-1-yl)methyl]-4H-4-carbazol-4-one A solution of 2,3-dichloro-5,6-dicyano-1,4-benzoquinone (80 mg) in dry tetrahydrofuran (1.5 ml) was added dropwise under nitrogen to a stirred, ice-cooled suspension of the product from Preparation 5 (100 mg) in a mixture of tetrahydrofuran (3.5 ml) and water (0.4 ml). The resultant blue solution was stirred for 1.5 h, and then the red suspension was concentrated in vacuo. Column chromatography of the residual solid eluting with a mixture of dichloromethane, ethanol and 0.88 ammonia (150:10:1) afforded the title compound as a white solid (0.47 g) m.p. 227.5°–229°. This material was identical to the product from Example 7 by t.l.c. and n.m.r.

EXAMPLE 21

3S-1,2,3,9-Tetrahydro-3-[(2-methylimidazol-1-yl)methyl]-9-methyl-4H-carbazol-4-one maleate A solution of the product from Example 7 (0.5 g) was dissolved in hot methanol (30 ml) and treated with a hot solution of (+)-di-p-toluoyl-D-tartaric acid monohydrate (0.7 g) in methanol (10 ml) and the resulting solution allowed to crystallise overnight to give the desired salt (0.68 g). This salt was dissolved in hot dimethylformamide (DMF, 20 ml), diluted with hot water (10 ml) and allowed to crystallise overnight. The product was filtered off, and dried in vacuo to give ca 90% enantiomerically pure (as shown by n.m.r.) (+)-di-p-toluoyl-D-tartaric acid salt (0.23 g) m.p. 231°–233°. A sample of the salt (0.15 g) was paritioned between 8% sodium bicarbonate (25 ml) and chloroform (2×25 ml). The combined extracts were dried and evaporated in vacuo to give pure free base (0.07 g). The base was dissolved in methanol (5 ml) acidified with maleic acid (0.03 g) and the salt precipitated by adding excess dry ether (80 ml) to give the title compound (0.062 g) m.p. 142°–145°.

T.l.c. Silica, dichloromethane/ethanol/0.88 ammonia (100:8:1) Rf 0.3 detection u.v. and iodoplatinic acid, identical to the product from Example 7. The enantiomer ratio, determined by $^1H$ n.m.r. was 93:7 (S:R). A sample of the maleate salt showed no significant optical rotation in methanol. The free base, regenerated from the maleate salt gave $[\alpha]_D^{25} -14°$ (c 0.19, MeOH).

EXAMPLE 22

3R-1,2,3,9-Tetrahydro-9-methyl-3-[(2-methyl-1H-imidazol-1yl)methyl]-4H-carbazol-4-one maleate A solution of the product from Example 7 (0.5 g) was dissolved in hot methanol (30 ml) was treated with a hot solution of (−)-di-p-toluoyl-L-tartaric acid monohydrate (0.7 g) in methanol (10 ml) and the resulting solution allowed to crystallise overnight to give the desired salt (0.8 g). This salt was dissolved in hot dimethylformamide (DMF, 20 ml), diluted with hot water (10 ml) and allowed to crystallise for 3 days. The product was filtered off, and dried in vacuo to give ca 95% enantiomerically pure (as shown by n.m.r.) (−)-di-p-toluoyl-L-tartaric salt (0.26 g) m.p. 170°–172°. A sample of the salt (0.2 g) was partitioned between 8% sodium bicarbonate (25 ml) and chloroform (2×25 ml). The combined extracts were dried and evaporated in vacuo to give pure free base (0.12 g). The base was dissolved in methanol (5 ml) acidified with maleic acid (0.045 g) and the salt precipitated by adding excess dry ether (80 ml) to give the title compound (0.08 g) m.p. 142°–145°.

T.l.c. Silica, dichloromethane/ethanol/0.88 ammonia (100:8:1) Rf 0.3 detection u.v. and iodoplatinic acid, identical to the product from Example 7. The enantiomer ratio, determined by $^1H$ n.m.r. was >95:5. A sample of the maleate salt showed no significant optical rotation in methanol. The free base, regenerated from the maleate salt, gave $[\alpha]_D^{24} +16°$ (c 0.34, MeOH).

EXAMPLE 23

9-[(Cyclopropyl)methyl]-1,2,3,9-tetrahydro-3-[(2-methyl-1H-imidazol-1-yl)methyl]-4H-carbazol-4-one, hydrochloride Sodium hydride (80% disp. in oil 0.075 g) was added to a solution of the product from Preparation 6 (0.7 g) in dimethylformamide (20 ml) and stirred for 15 min. (Bromomethyl)cyclopropane (0.33 g) was added and the solution maintained at 40° for 4 h. before partitioning between aqueous sodium carbonate (2N, 100 ml) and ethyl acetate (2×50 ml). The combined organic extracts were washed with water (50 ml), dried and evaporated in vacuo to give an oil which was purified by column chromatography (B) to give pure free base. A solution of the free base in ethanol (15 ml) was acidified with ethereal hydrogen chloride and diluted with dry ether to precipitate the title compound (0.4 g) m.p. 120°–130°;

N.m.r. δ($CD_3SOCD_3$) 0.4–0.6 (4H,m,cyclopropyl-$CH_2CH_2$—), 1.2–1.3 (1H,m,cyclopropyl-C$\underline{H}$—) 2.7 (3$\underline{H}$,s,—$CH_3$), 4.29 and 4.69 (2H, A$\underline{BX}$,CHC$\underline{H}_2$N) and 7.2–8.1 (6$\underline{H}$,m,aromatic).

Analysis—Found: C,63.6;H,6.55;N,10.5. $C_{21}H_{23}N_3O.HCl.1.5H_2O$ requires C,63.5;H,6.8;N,10.6%.

EXAMPLE 24

1,2,3,9-Tetrahydro-3-[(2-methyl-1H-imidazol-1-yl)methyl]-9-(2-propynyl-4H-carbazol-4-one, oxalate Sodium hydride (80% disp. in oil, 0.075 g) was added to a solution of the product from Preparation 6 (0.7 g) in dimethylformamide (10 ml) and stirred for 15 min. Propargyl bromide (0.44 g) was added and the solution maintained at 40° for 5 h before partitioning between aqueous sodium carbonate (2N, 100 ml) and ethyl acetate (2×50 ml). The combined organic layers were washed with water (2×50 ml), dried and evaporated in vacuo to give an oil which was purified by chromatography (B) to give a solid. This solid was dissolved in ethanol (10 ml) and a solution of oxalic acid (0.14 g) in methanol (5 ml) added. Addition of dry ether precipitated the title compound (0.35 g) m.p. 237°–238°.

N.m.r. δ($CD_3SOCD_3$), 2.60 (3H,s,$CH_3$), 3.47 (1H,t,C≡C—$\underline{H}$), 4.25 and 4.65 (2H, A$\underline{BX}$ $\overline{CH}CH_2N$), 5.19 (2H,d,NC$\underline{H}_2$C≡C), and 7.2–8.1 ($\overline{6H}$,m,aromatic).

Analysis—Found: C,64.0; H, 5.0; N, 10.0. $C_{20}H_{19}N_3O.C_2H_2O_4.3H_2O$ requires C, 63.9; H, 5.1; N, 10.2%.

EXAMPLE 25

9-(Cyclobutylmethyl)-1,2,3,9-tetrahydro-3-[(2-methyl-1H-imidazol-1-yl)methyl]-4$\underline{H}$-carbazol-4-one maleate A solution of 1,2,3,9-tetrahydro-3-[(2-methyl-1$\underline{H}$-imidazol-1-yl)methyl]-4$\underline{H}$-carbazol-4-one (1.00 g) in dry dimethylformamide (10 ml) was added dropwise under nitrogen to a stirred suspension of sodium hydride (78% in oil; 0.12 g) in dry dimethylformamide (5 ml). The mixture was stirred for 1.5 h and a solution of cyclobutanemethanol (4-methylbenzenesulphonate) (2.35 g) in dry dimethylformamide (5 ml) was added. The solution was heated to 50°, stirred for 3.25 h, allowed to cool and concentrated in vacuo to ca 10 ml. The residual solution was poured onto water (100 ml) and extracted with ethyl acetate (3×100 ml). The combined extracts were washed with water (5×70 ml) and brine (70 ml), dried ($Na_2SO_4$) and concentrated in vacuo.

Flash chromatography (C) of the residual gum afforded a foam (0.67 g). A portion of this material (0.47 g) was dissolved in boiling absolute ethanol (2 ml) and a solution of maleic acid (0.15 g) in refluxing absolute ethanol (1 ml) was added. The stirred solution was diluted with dry ether (50 ml) and the resultant solid filtered off, washed with dry ether (3×15 ml) and dried in vacuo at 60° for 21 h to give the title compound as a solid (0.54 g) m.p. 125°–127°.

Analysis—Found: C, 66.3; H, 6.3; N, 8.8. $C_{22}H_{25}N_3O.C_4H_4O_4.0.58H_2O$ requires C, 65.9; H, 6.4; N, 8.9%.

N.m.r. δ(DMSO) includes 1.7–2.2 (8H,m,cyclobutane and H-2 ax); 2.65 (3H,s,Ar—$CH_3$); and 4.2–4.75 (4H,m,indole N—$CH_2$ and imidazole N—$CH_2$).

The following compounds were prepared according to the method of Example 3, using the reaction conditions given in Table IV hereinafter.

EXAMPLE 26

9-(Cyclopentylmethyl)-1,2,3,9-tetrahydro-3-[(2-methyl-1H-imidazol-1-yl)methyl]-4$\underline{H}$-carbazol-4-one maleate m.p. 107°–108°.

Analysis—Found: C, 65.2; H, 6.55; N, 8.2. $C_{23}H_{27}N_3O.C_4H_4O_4.H_2O$ requires C, 65.4; H, 6.7; N, 8.5%.

N.m.r. δ(DMSO) includes 1.2–2.45 (11H,m,cyclopentane and H-2); 2.65 (3H,s,Ar—$CH_3$); 4.17 (2H,d,N—$CH_2$-cyclopentane); and 4.27, 4.66 (2H,A$\underline{BX}$, imidazole NC$\underline{H}_2$).

EXAMPLE 27

1,2,3,9-Tetrahydro-3-[(2-methyl-1H-imidazol-1-yl)methyl]-9-(2-octynyl)-4$\underline{H}$-carbazol-4-one, maleate m.p. 115°–116°.

Analysis—Found: C, 69.2; H, 6.6; N, 8.3. $C_{25}H_{29}N_3O.C_4H_4O_4$ requires C, 69.2; H, 6.6; N, 8.3%.

N.m.r. δ($CDCl_3$) includes 0.85 (3H,t,≡C($CH_2)_4CH_3$); 1.2–1.52 (6H,m,≡C—$CH_2CH_2CH_2CH_2CH_3$); 2.8 (3H,s,Ar—$CH_3$); $\overline{4.53}$ (2$\overline{H}$,A$\underline{BX}$,CHC$\underline{H}_2$N); and 4.80 (2H,t,NC$\underline{H}_2$C≡).

EXAMPLE 28

-(3-Cyclopentylpropyl)-1,2,3,9-tetrahydro-3-[(2-methyl-1H-imidazol-1-yl) methyl]-4$\underline{H}$-carbazol-4-one, maleate m.p. 119°–120.5°.

Analysis—Found: C, 69.1; H, 7.2; N, 8.3. $C_{25}H_{31}N_3O_4.C_4H_4O_4$ requires C, 68.9; H, 7.0; N, 8.3%.

N.m.r. δ($CDCl_3$) includes 0.95–1.85 (13 H, cyclopentane and $CH_2CH_2CH$); 2.80 (3H,s,Ar—$CH_3$); 4.08 (2H,t,NC$\underline{H}_2CH_2$); and 4.55 (2H,A$\underline{B}$x, NC$\underline{H}_2CH$).

EXAMPLE 29

9-(Cycloheptylmethyl)-1,2,3,9-tetrahydro-3-[(2-methyl-1H-imidazol-1-yl)methyl]-4$\underline{H}$-carbazol-4-one, maleate Analysis—Found: C, 66.6; H, 7.0; N, 7.7. $C_{25}H_{31}N_3O.1.5C_4H_4O_4$ requires C, 66.1; H, 6.6; N, 7.5%.

N.m.r. δ($CDCl_3$) includes 1.15–1.75 (12H,m,cycloheptane $CH_2$); 2.80 (3H,s,Ar—$CH_3$); 3.92 (2H,d,NC$\underline{H}_2$-cycloheptane); and 4.56 (2H, A$\underline{BX}$,NC$\underline{H}_2$CH).

TABLE IV

| | | | ALKYLATION | | | | | | SALT FORMATION (MALEATE) | | |
|---|---|---|---|---|---|---|---|---|---|---|---|
| Ex. No. | Starting material (g) | NaH (g) | Alkylating agent Structure | Weight (g) | Reaction time (h) | Reaction temp. (°C.) | Eluent | Yield of base (g) | Wt. of base (g) | Wt. of acid (g) | Yield (g) |
| 26 | 1.0 | 0.12 | ⌬—CH₂OTos | 2.0 | 0.75 + 4.0 | 55 | C | 1.0 | 0.4 | 0.32 | 1.08 |
| 27 | 0.5 | 0.062 | BrCH₂C≡CC₅H₁₁ | 0.378 | 0.25 + 6 60 | RT 4-5 | D | 0.590 | 0.590 | 0.194 | 0.648 |
| 28 | 0.5 | 0.062 | ⌬—(CH₂)₃Br | 0.378 | 0.25 + 24 | RT | C | 0.615 | 0.615 | 0.203 | 0.507 |
| 29 | 0.2 | 0.024 | ⬡—CH₂Br | 0.151 | 0.25 + 20 | RT | C | 0.136 | 0.136 | 0.045 | 0.095 |

Tos = p-toluenesulphonyl
RT = room temperature

We claim:

1. A compound of formula (I)

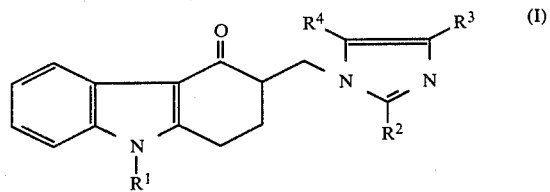

wherein $R^1$ represents a hydrogen atom or a $C_{1-10}$ alkyl, $C_{3-7}$ cycloalkyl, $C_{3-6}$ alkenyl, $C_{3-7}$ cycloalkyl-($C_{1-4}$)alkyl, $C_{3-10}$ alkynyl, phenyl or phenyl-$C_{1-3}$ alkyl group, and one of the groups represented by $R^2$, $R^3$ and $R^4$ is a hydrogen atom or a $C_{1-6}$alkyl, $C_{3-7}$ cycloalkyl, $C_{2-6}$ alkenyl or phenyl-($C_{1-3}$) alkyl group and each of the other two groups, which may be the same or different, represents a hydrogen atom or a $C_{1-6}$ alkyl group; or a physiologically acceptable salt or solvate thereof.

2. A compound according to claim 1 in which one of the groups represented by $R^2$, $R^3$ and $R^4$ represents a $C_{1-3}$ alkyl, $C_{3-6}$ cycloalkyl or $C_{3-6}$ alkenyl group and each of the other two groups, which may be the same or different represents a hydrogen atom or a $C_{1-3}$ alkyl group.

3. A compound according to claim 1 in which $R^1$ represents a hydrogen atom or a $C_{1-6}$ alkyl, $C_{5-6}$ cycloalkyl or $C_{3-4}$ alkenyl group and either $R^2$ represents a hydrogen atom and $R^3$ and/or $R^4$ represents a $C_{1-3}$ alkyl group or $R^2$ represents a $C_{1-3}$ alkyl group and both $R^3$ and $R^4$ represent hydrogen atoms.

4. A compound of formula (I)

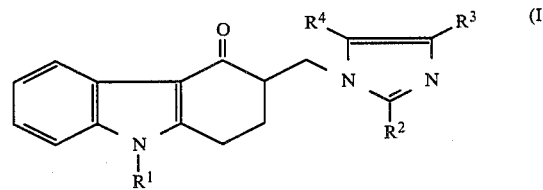

wherein $R^1$ represents a hydrogen atom or a $C_{1-10}$ alkyl, $C_{3-7}$ cycloalkyl, $C_{3-6}$ alkenyl, phenyl or phenyl-$C_{1-3}$ alkyl group; and one of the groups represented by $R^2$, $R^3$ and $R^4$ is a hydrogen atom or a $C_{1-6}$ alkyl, $C_{3-7}$ cycloalkyl, $C_{2-6}$ alkenyl or phenyl($C_{1-3}$) alkyl group and each of the other two groups, which may be the same or different, represents a hydrogen atom or a $C_{1-6}$ alkyl group; or a physiologically acceptable salt or solvate thereof.

5. A compound according to claim 4 in which $R^1$ represents a hydrogen atom or a $C_{1-6}$ alkyl, $C_{3-6}$ cycloalkyl or $C_{3-6}$ alkenyl group.

6. A compound according to claim 4 in which one of the groups represented $R^2$, $R^3$ and $R^4$ represents a $C_{1-3}$ alkyl, $C_{3-6}$ cycloalkyl or $C_{3-6}$ alkenyl group and each of the other two groups, which may be the same or different, represents a hydrogen atom or a $C_{1-3}$ alkyl group.

7. A compound according to claim 4 in which $R^1$ represents a hydrogen atom or a $C_{1-6}$ alkyl, $C_{5-6}$ cycloalkyl or $C_{3-4}$ alkenyl group and either $R^2$ represents a hydrogen atom and $R^3$ and/or $R^4$ represents a $C_{1-3}$ alkyl group or $R^2$ represents a $C_{1-4\,3}$ alkyl group and $R^3$ and $R^4$ both represent hydrogen atoms.

8. A compound of formula (Ia)

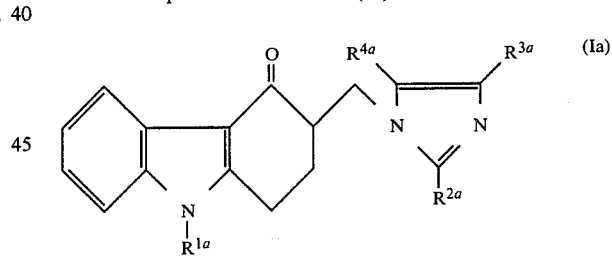

wherein $R^{1a}$ represents a hydrogen atom or a methyl, ethyl, propyl, prop-2-yl, prop-2-enyl or cyclopentyl group; $R^{3a}$ represents a hydrogen atom; and either $R^{2a}$ represents a methyl, ethyl, propyl or prop-2-yl group and $R^{4a}$ represents a hydrogen atom or $R^{2a}$ represents a hydrogen atom and $R^{4a}$ represents a methyl or ethyl group; or a physiologically acceptable salt or solvate thereof.

9. 1,2,3,9-Tetrahydro-9-methyl-3-[(2-methyl-1H-imidazol-1-yl)methyl]-4H-carbazol-4-one or a physiologically acceptable salt or solvate thereof.

10. 1,2,3,9-Tetrahydro-3-[(2-methyl-1H-imidazol-1-yl)-methyl]-9-(prop-2-enyl)-4H-carbazol-4-one; 9-Cyclopentyl-1,2,3,9-tetrahydro-3-[(2-methyl-1H-imidazol-1-yl)methyl]-4H-carbazol-4-one; 1,2,3,9-Tetrahydro-3-[2-methyl-1H-imidazol-1-yl)methyl]-9-(prop-2-yl)-4H-carbazol-4-one; or a physiologically acceptable salt or solvate thereof.

11. A pharmaceutical composition for the treatment of a condition caused by disturbance of "neuronal" 5HT function comprising at least one compound of formula (I) as defined in claim 1 or a physiologically acceptable salt or solvate thereof in an amount effective to relieve said condition together with at least one physiologically acceptable carrier or exipient.

12. A method of treating a condition caused by disturbance of "neuronal" 5HT function which comprises administering to a patient an effective amount of a compound of formula (I) as defined in claim 1 or a physiologically acceptable salt or solvate thereof to relieve said condition.

13. The compound of claim 9 in the form of a hydrochloride salt.

14. The compound of claim 9 in the form of the hydrochloride dihydrate.

15. A pharmaceutical composition according to claim 11 in which said compound of formula (I) is 1,2,3,9-tetrahydro-9-methyl-3-[(2-methyl-1H-imidazol-1-yl)methyl]-4-H-carbazol-4-one or a physiologically acceptable salt or solvate thereof.

16. A pharmaceutical composition according to claim 15 in which said compound is present as a hydrochloride salt.

17. A pharmaceutical composition according to claim 15 in which said compound is present as the hydrochloride dihydrate.

18. A method according to claim 12 in which said compound of formula (I) is 1,2,3,9-tetrahydro-9-methyl-3-[(2-methyl-1H-imidazol-1yl)methyl]-4H-carbazol-4-one or a physiologically acceptable salt or solvate thereof.

19. A method according to claim 18 in which said compound is used as a hydrochloride salt.

20. A method according to claim 18 in which said compound is used as the hydrochloride dihydrate.

* * * * *

UNITED STATES PATENT AND TRADEMARK OFFICE

CERTIFICATE EXTENDING PATENT TERM UNDER 35 U.S.C. 156

Patent No.    : 4,695,578

Dated         : September 22, 1987

Inventor(s)   : Ian H. Coates et al

Patent Owner  : Glaxo Group Ltd.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

104 DAYS with all rights pertaining thereto as provided by 35 U.S.C. 156 (b).

I have caused the seal of the Patent and Trademark Office to be affixed this 30th day of December, 1991.

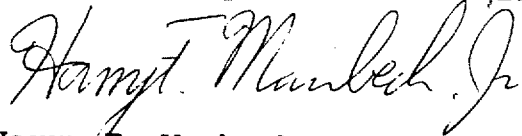

Harry F. Manbeck, Jr.
Assistant Secretary and Commissioner of Patents and Trademarks